(12) United States Patent
Valois et al.

(10) Patent No.: US 9,603,748 B2
(45) Date of Patent: Mar. 28, 2017

(54) COMPRESSION ORTHOSIS

(75) Inventors: Christophe Valois, Montmerle (FR);
Michael McGowan, Montbonnot Saint Martin (FR)

(73) Assignee: GIBAUD, Saint-Etienne (FR)

( * ) Notice: Subject to any disclaimer, the term of this patent is extended or adjusted under 35 U.S.C. 154(b) by 864 days.

(21) Appl. No.: 13/819,522

(22) PCT Filed: Jul. 12, 2011

(86) PCT No.: PCT/FR2011/051656
§ 371 (c)(1),
(2), (4) Date: Sep. 30, 2013

(87) PCT Pub. No.: WO2012/028795
PCT Pub. Date: Mar. 8, 2012

(65) Prior Publication Data
US 2014/0024990 A1    Jan. 23, 2014

(30) Foreign Application Priority Data
Aug. 30, 2010    (FR) ...................... 10 56837

(51) Int. Cl.
*A61F 13/08* (2006.01)
*D04B 1/26* (2006.01)
*A41B 11/02* (2006.01)

(52) U.S. Cl.
CPC .............. *A61F 13/08* (2013.01); *D04B 1/265* (2013.01); *A41B 11/02* (2013.01); *D10B 2403/02* (2013.01)

(58) Field of Classification Search
CPC ...... A61F 13/061; A61F 13/107; A61F 13/08; A61F 5/0106; A41B 11/00; A41B 11/002; A41B 11/02; D04B 1/26; D04B 1/265; D10B 2403/02
See application file for complete search history.

(56) References Cited

U.S. PATENT DOCUMENTS

| | | |
|---|---|---|
| 3,162,029 A | 12/1964 | Laws et al. |
| 4,149,274 A | 4/1979 | Garrou et al. |
| 4,237,707 A | 12/1980 | Safrit et al. |
| 4,282,726 A | 8/1981 | Wilkins |
| 4,702,091 A | 10/1987 | Good et al. |

FOREIGN PATENT DOCUMENTS

| | | |
|---|---|---|
| DE | 86 06 402 U1 | 4/1986 |
| FR | 2 445 701 A1 | 8/1980 |

OTHER PUBLICATIONS

International Search Report issued in PCT/FR2011/051656, Sep. 8, 2011.

*Primary Examiner* — Ophelia A Hawthorne
(74) *Attorney, Agent, or Firm* — Workman Nydegger

(57) ABSTRACT

A compression orthosis for a lower limb includes a compression knit having at least one honeycomb area defined by a knit with a first type of mesh interconnecting elastic knitting yarns, non-elastic knitting yarns and elastic weft threads, and a second type of mesh. The structure is defined by elastic knitting yarns having meshes extending over at least two rows. The elastic weft yarns have floats of at least two needles, and the non-elastic knitting yarns have floats of at least one needle.

19 Claims, 4 Drawing Sheets

COMPRESSION ORTHOSIS

BACKGROUND

The present invention relates to a compression orthosis, in particular a stocking, pantyhose or support sock.

Wearing these orthoses is prescribed in case of venous insufficiency, and more particularly in case of superficial venous insufficiency.

In these cases, the blood flow no longer occurs under satisfactory conditions; the blood stagnates and the superficial veins expand.

Aside from phlebology-based medicinal treatments, venous insufficiency can be treated orthopedically by pantyhose, stockings or compression socks that apply tapering pressure on the lower limb. Highly elastic compression orthoses make it possible to escalate the blood toward the heart through greater pressure on the ankle than at the calf or thigh.

Out of functional necessity, contention orthoses are made from a highly elastic textile material, and the comfort thereof needs improvement. Wearing of a contention orthosis will be better observed when the orthosis is more comfortable.

In that context, the aim of the invention is to propose a compression orthosis that has improved comfort without deteriorating its compression properties or making it more expensive to manufacture.

SUMMARY

The invention relates to a compression orthosis for a lower limb, characterized in that the compression orthosis comprises at least one honeycomb area defined by a knit having:
- a first type of mesh interconnecting elastic knitting yarns, non-elastic knitting yarns and elastic weft yarns, and
- a second type of mesh wherein the structure is defined by the fact that:
  - the elastic knitting yarns have meshes extending over at least two rows,
  - the elastic weft yarns have floats of at least two needles, and
  - the non-elastic knitting yarns have floats of at least one needle.

The invention thus proposes an original structure in a particular area of an orthosis so as to create a honeycomb whereof the thickness will provide increased comfort. It should be noted that the honeycomb is an integral part of the knit making up the orthosis.

In one preferred embodiment, in the honeycomb area, the elastic knitting yarns extend over six rows.

In one preferred embodiment, in the honeycomb area, the elastic weft yarns have floats for three needles.

In one preferred embodiment, in the honeycomb area, the non-elastic knitting yarns have floats for one needle.

Furthermore, the first type of mesh can be a laid-in jersey.

According to preferred arrangements of the invention:
- the elastic knitting yarn is a covered spandex;
- the non-elastic knitting yarn is a polyamide;
- the elastic weft yarn is a double-covered spandex.

In one particularly advantageous application of the invention, the honeycomb area is positioned at the sole of an orthosis of the group in particular comprising a sock, half-hose, a stocking, or pantyhose.

BRIEF DESCRIPTION OF THE DRAWINGS

For proper understanding of the invention, the invention is described in reference to the appended drawing showing one embodiment of a contention sock according to said invention.

DETAILED DESCRIPTION OF VARIOUS EMBODIMENTS

Figure 1:
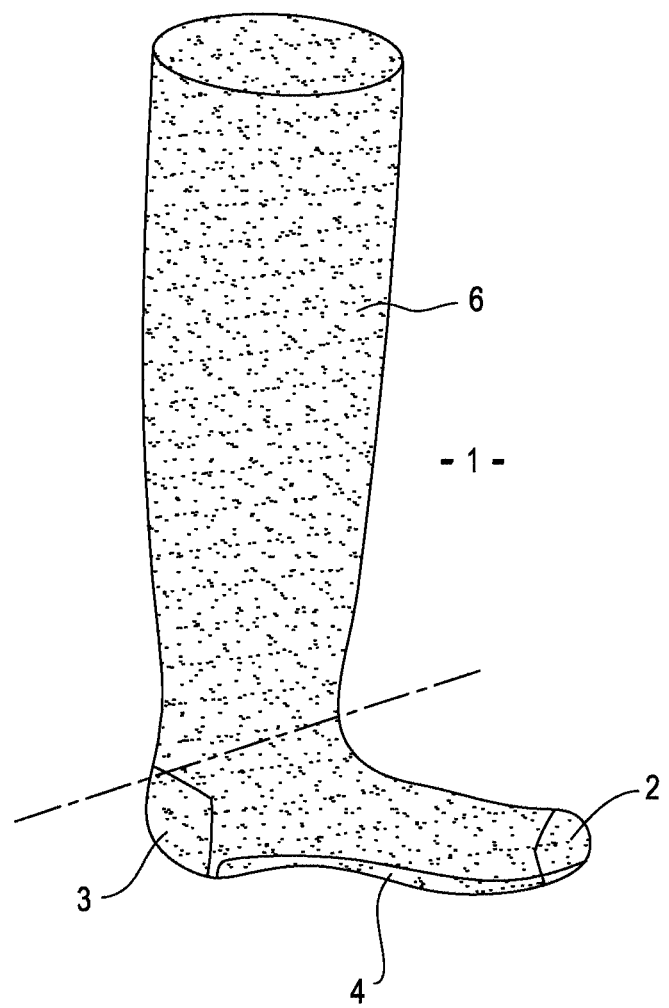
FIG. 1 diagrammatically shows a sock according to the invention.

FIG. 1 generally shows a sock bearing reference 1. This is a tubular compression orthosis made from a knit textile. The yarns involved in the knit and the mesh structure are determined so that the sock exerts a tapered contention on the limb once the sock is placed thereon.

The sock 1 shown in FIG. 1 is of the half-hose type and thus comprises a portion that surrounds the foot and a portion that surrounds the ankle and the calf.

In a known manner, this sock 1 is designed to produce a pressure of 10 mm Hg (minimum for a class 1 orthosis) to 36 mm Hg (minimum for a class 4 orthosis)—the mm Hg being the typical unit of measure in phlebology—measured at the ankle.

The sock 1 has a conventional compression knit that makes it possible to offer the required contention.

It is possible for the sock 1 to have a smooth, ribbed or optionally mottled appearance.

As is also typical, a particular treatment may be reserved for the front 2 and rear 3 ends of the foot.

On the parts of the sock that surround the ankle and the heel and on the upper part of the foot, the knit is conventional and can be made of laid-in jersey meshes.

Figure 4:
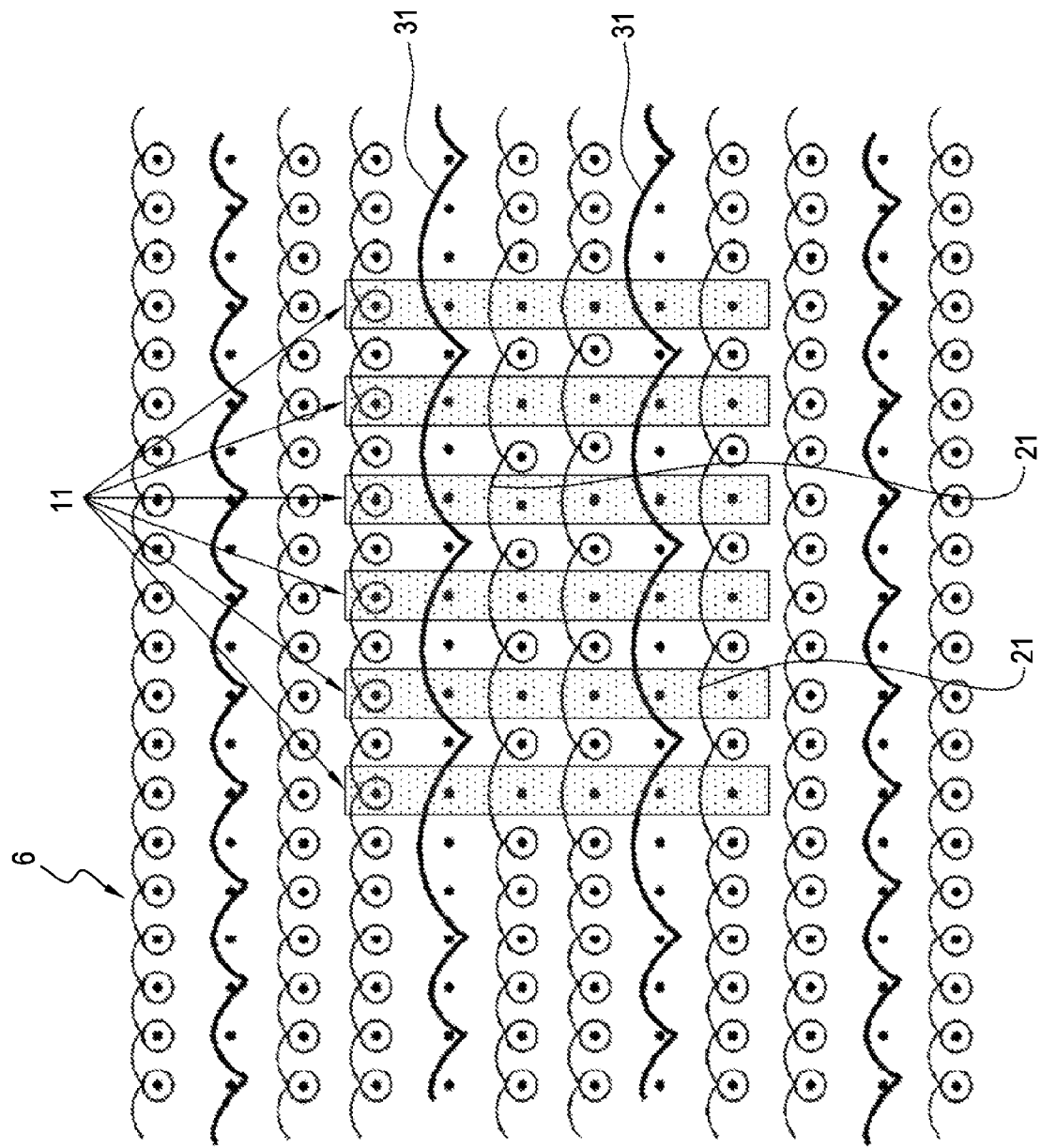
FIG. 4 shows a structural diagram of the sole portion of the sock of FIGS. 1 to 3.

It is also provided with an original knit that is shown in FIG. 4. The knit includes:
- a first elastic knitting yarn 10 for example made from polyamide and/or cotton-covered spandex;
- a second non-elastic knitting yarn 20 for example made from polyamide;
- an elastic weft yarn 30 that produces elastic pressure for example, made from spandex or with a base of a covered spandex mixture (for example, polyamide).

One important aspect of the invention is the treatment of the sole portion 4 of the sock 1, i.e., the part of the sock 1 that is across from the foot sole.

The sole portion 4 of the sock 1 is not an attached part, but is made during the knitting sequence of the sock 1.

A substantial modification is thus provided to the mesh that makes up the sole portion 4 of the sock 1.

The mesh weave of the sole portion 4 of the sock 1 is completely original.

In this portion of the sock 1, two combined original arrangements are shown that appear in the structure diagram of FIG. 4.

On the one hand, the elastic knitting yarns 10 are knitted in elongated meshes 11 over several rows. In practice, the meshes can extend over six rows. The elongated meshes 11 are shown conventionally in gray on the structure diagram. Concretely, these elongated meshes 11 are produced by putting loaded needles 40 on standby. Thus, the meshes waiting on the loaded needles 40 extend to form floating yarns. The elongated meshes appear on right-side outside of the sole 4.

On the other hand, the weft yarns 30 have floats 31 for three at the intersection with the elongated meshes. Outside the elongated mesh area 11, the weft yarns 30 have a float for one needle in a first mesh area 6.

Furthermore, the non-elastic knitting yarns 20 have floats 21, as shown in FIG. 4, for one needle at the intersection with the elongated meshes. Outside the elongated mesh area 11, the non-elastic knitting yarns 20 have an all-needle jersey in the first mesh area 6.

The combined effect of the elongated meshes 11 of the elastic knitting yarns 30 and the floats 31 of the elastic weft yarns 10 and the floats 21 of the non-elastic yarns 20 has the remarkable effect of creating a honeycomb area 5 effect on the sole of the sock 1.

In fact, during production of the sock 1, the elastic knitting yarn 10, the non-elastic knitting yarn 20 and the elastic weft yarn 30 are kept stressed in the knitting machine.

However, upon leaving the machine, the elastic knitting yarns 10, the non-elastic knitting yarns 20 and the elastic weft yarns 30 are no longer kept extended and assume their normal contracted state while creating hollows and raised portions.

In the illustrated example, the honeycomb area 5 is present in the sole at the heel and the ball of the foot, which are the main bearing points of the body.

This honeycomb area 5 imparts an excess thickness to the sole of the sock 1, which is extremely comfortable to wear and thus has a beneficial effect on observance of the wear of the contention sock 1. The honeycomb area 5 in fact absorbs part of the body weight.

The honeycomb appears distinctly on the "right-side out" surface of the sole, on which an array of raised portions and hollows with essentially square contours essentially generated by the elongated meshes of the elastic knitting yarns is present, while the inside surface of the sole shows a series of parallel ripples essentially generated by the floats of the elastic weft yarns 30.

Figure 2:
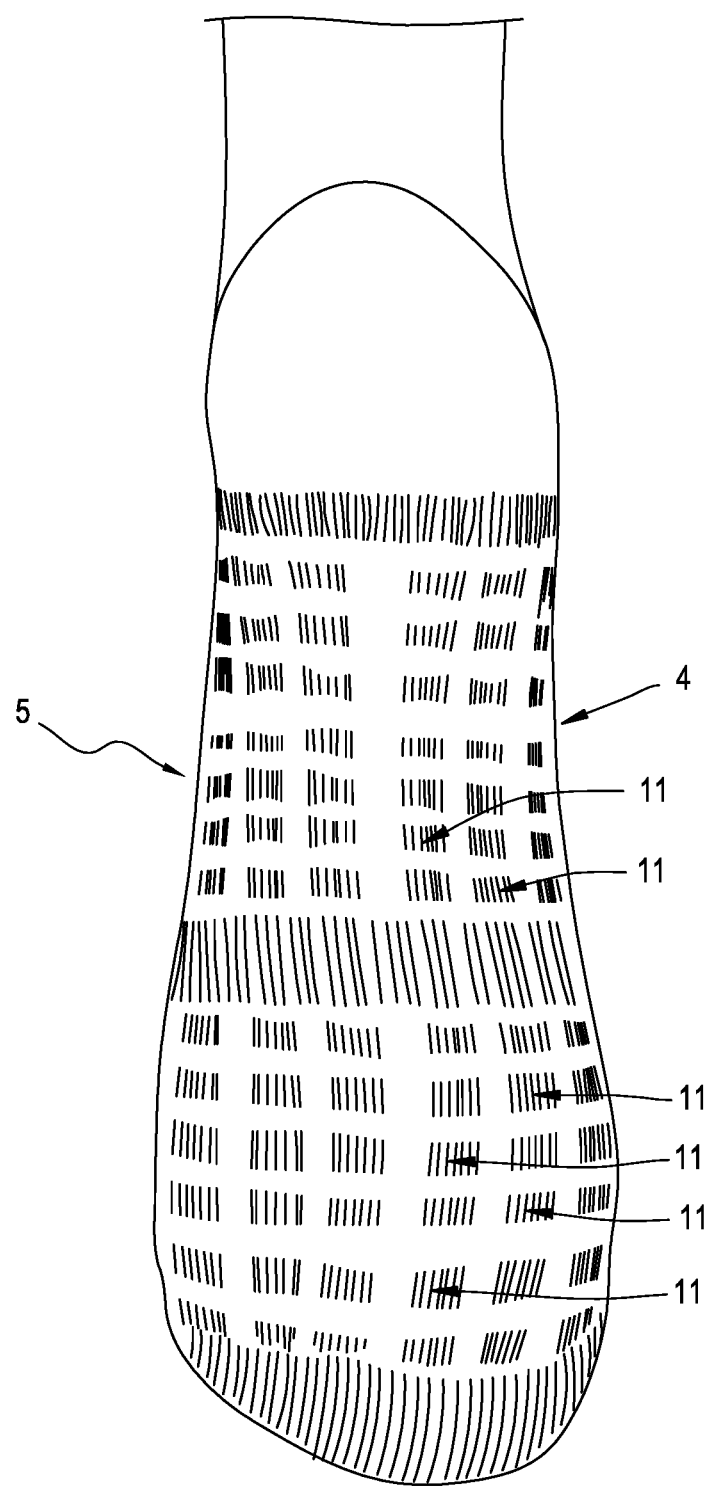
FIGS. 2 and 3 show the sole portion of said sock from below and the side.
Figure 3:
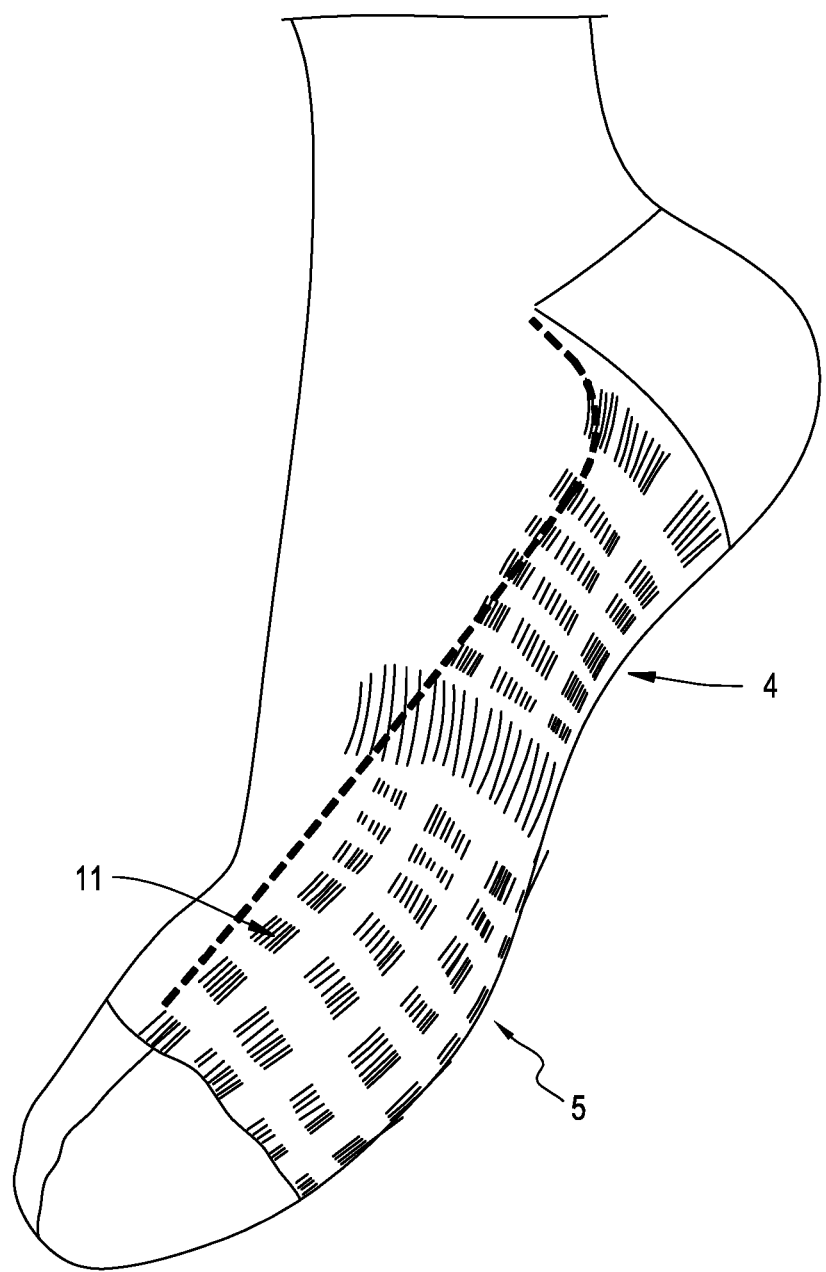

As shown in FIG. 2 or FIG. 3, series of six elongated meshes form protrusions that alternate transversely with series of six jersey meshes that form hollows.

One very interesting point that bears mentioning is that the honeycomb sole area 4 that is specific to the invention can be incorporated into any type of contention orthosis. In other words, the honeycomb area is compatible with any type of elastic venous compression. Thus, it can be considered to create a honeycomb area in orthoses belonging to the usual classes I, II, III or IV.

Another point that should be stressed is that the honeycomb area can be positioned in areas other than the sole area of an orthosis. Thus, the honeycomb area could be situated at a joint to provide extra comfort in a particular area.

Of course, the invention is not limited to the embodiment described above as a non-limiting example, but on the contrary encompasses all embodiments thereof.

The invention claimed is:

1. A compression orthosis for a lower limb, wherein the compression orthosis comprises at least one honeycomb area defined by a knit having:
   a first mesh area having interconnecting elastic knitting yarns, non-elastic knitting yarns and elastic weft yarns, and
   a second mesh area having a structure wherein:
      the elastic knitting yarns have meshes extending over at least two rows,
      the elastic weft yarns have floats of at least two needles, and
      the non-elastic knitting yarns have floats of at least one needle.

2. The compression orthosis according to claim 1, wherein, in the honeycomb area, the elastic knitting yarns extend over six rows.

3. The compression orthosis according to claim 2, wherein in the honeycomb area, the elastic weft yarns have floats for three needles.

4. The compression orthosis according to claim 2, wherein in the honeycomb area, the non-elastic knitting yarns have floats for one needle.

5. The compression orthosis according to claim 2, wherein the first type of mesh is an all needle laid-in jersey.

6. The compression orthosis according to claim 2, wherein the elastic knitting yarn is a covered spandex.

7. The compression orthosis according to claim 1, wherein in the honeycomb area, the elastic weft yarns have floats for three needles.

8. The compression orthosis according to claim 7, wherein in the honeycomb area, the non-elastic knitting yarns have floats for one needle.

9. The compression orthosis according to claim 7, wherein the first type of mesh is an all needle laid-in jersey.

10. The compression orthosis according to claim 7, wherein the elastic knitting yarn is a covered spandex.

11. The compression orthosis according to claim 1, wherein in the honeycomb area, the non-elastic knitting yarns have floats for one needle.

12. The compression orthosis according to claim 11, wherein the first type of mesh is an all needle laid-in jersey.

13. The compression orthosis according to claim 11, wherein the elastic knitting yarn is a covered spandex.

14. The compression orthosis according to claim 1, wherein the first type of mesh is an all needle laid-in jersey.

15. The compression orthosis according to claim 14, wherein the elastic knitting yarn is a covered spandex.

16. The compression orthosis according to claim 1, wherein the elastic knitting yarn is a covered spandex.

17. The compression orthosis according to claim 1, wherein the non-elastic knitting yarn is a polyamide.

18. The compression orthosis according to claim 1, wherein the elastic weft yarn is a double-covered spandex.

19. The compression orthosis according to claim 1, wherein the honeycomb area is positioned at a sole of an orthosis selected from the group consisting of a sock, half-hose, a stocking, and pantyhose.

* * * * *